US008349377B2

(12) United States Patent
Piccirilli et al.

(10) Patent No.: US 8,349,377 B2
(45) Date of Patent: *Jan. 8, 2013

(54) MEDICAMENT COMPRISING A PEPTIDE EXTRACT OF AVOCADO, WHICH IS INTENDED FOR THE TREATMENT AND PREVENTION OF ILLNESSES THAT ARE LINKED TO AN IMMUNE SYSTEM DEFICIENCY

(75) Inventors: Antoine Piccirilli, Versailles (FR); Nathalie Piccardi, Arceau (FR); Philippe Msika, Versailles (FR); François Paul, Toulouse (FR); Stéphanie Bredif, Chaudon (FR)

(73) Assignee: Laboratoires Expanscience, Courbevoie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/923,819

(22) Filed: Oct. 8, 2010

(65) Prior Publication Data
US 2011/0082070 A1 Apr. 7, 2011

Related U.S. Application Data

(63) Continuation of application No. 11/587,960, filed as application No. PCT/FR2005/001076 on Apr. 29, 2005, now Pat. No. 7,833,554.

(30) Foreign Application Priority Data

Apr. 30, 2004 (FR) ...................................... 04 04640

(51) Int. Cl.
*A61K 36/00* (2006.01)
(52) U.S. Cl. ........... 424/769; 424/777; 424/725; 514/23
(58) Field of Classification Search ........................ None
See application file for complete search history.

(56) References Cited

U.S. PATENT DOCUMENTS

| 5,384,147 | A * | 1/1995 | Hilpert ........................ 426/615 |
| 5,928,659 | A | 7/1999 | Moy |
| 6,146,616 | A | 11/2000 | Msika et al. |
| 6,348,271 | B1 | 2/2002 | Nakata et al. |
| 6,582,688 | B1 | 6/2003 | Broutin et al. |
| 6,861,077 | B1 | 3/2005 | Cannell et al. |
| 2004/0013753 | A1 | 1/2004 | Boumediene et al. |
| 2004/0018257 | A1 | 1/2004 | Boumediene et al. |
| 2004/0022882 | A1 | 2/2004 | Piccirilli et al. |
| 2006/0029685 | A1 * | 2/2006 | Henderson et al. ........... 424/729 |

FOREIGN PATENT DOCUMENTS

| DE | 19852508 A1 | 5/2000 |
| FR | 2787714 A1 | 6/2000 |
| FR | 2843027 A1 | 2/2004 |
| JP | 02135260 A | 5/1990 |
| WO | WO 98/47479 A1 | 10/1998 |
| WO | WO 99/43298 A1 | 9/1999 |
| WO | WO 01/21150 A1 | 3/2001 |
| WO | WO 01/21605 A2 | 3/2001 |
| WO | WO 01/68040 A2 | 9/2001 |

OTHER PUBLICATIONS

Kashman et al., "New Compounds from Avocado Pear," *Tetrahedron*, 1969, 25, 4617-4631.
Liu et al., "Human beta-defensin-2 production in keratinocytes is regulated by interleukin-1, bacteria, and the state of differentiation," Pub Med abstract, 2 pgs. (abstract as published in J. Invest. Dermatol., Feb. 2002, 118(2), 275-81.
Dvash et al., "Determination by Near-Infrared spectroscopy of Perseitol used as a Marker for the Botanical Origin of Avocado," *Journal of Agricultural and Food Chemistry*, vol. 50, pp. 5283-5287, 2002.
Perales et al., "Analysis of a avocado allergen (Prs a 1) IgE-binding peptides generated by simulated gastric fluid digestion," *Journal of Allergy Clinical Immunology*, vol. 112, No. 5, p. 12, 2003.
Notice of Allowance issued by the Examiner in U.S. Appl. No. 11/587,960 on Jul. 9, 2010.
Office Action issued by the Examiner in U.S. Appl. No. 11/587,960 on Oct. 27, 2009.
Office Action issued by the Examiner in U.S. Appl. No. 11/587,960 on Jun. 19, 2009.

* cited by examiner

*Primary Examiner* — Christopher R. Tate
*Assistant Examiner* — Deborah A. Davis
(74) *Attorney, Agent, or Firm* — Foley & Lardner LLP

(57) ABSTRACT

The invention relates to a medicament which comprises a peptide extract of avocado and which can also comprise a composition containing D-mannoheptulose and/or perseitol, such as a water-soluble extract of avocado sugars, and/or a peptide extract of lupine. The inventive medicament is intended for the treatment and/or prevention of illnesses that are linked to an alteration in innate and/or acquired immunity, through an increase in the production of anti-microbial peptides, preferably hBD-2, without inducing inflammatory reactions, irritations or intolerances.

21 Claims, No Drawings

MEDICAMENT COMPRISING A PEPTIDE EXTRACT OF AVOCADO, WHICH IS INTENDED FOR THE TREATMENT AND PREVENTION OF ILLNESSES THAT ARE LINKED TO AN IMMUNE SYSTEM DEFICIENCY

This invention relates to a drug comprising an avocado peptide extract, advantageously for the treatment and/or prevention of diseases which are linked to an immunodeficiency, and more particularly to a deterioration of natural immunity.

All animal species daily confront a number of microorganisms, such as bacteria, fungi, parasites or viruses, which may affect their health or even their survival. Two defense systems oppose these microorganisms: one which is called natural immunity, and is common to all animals, including man, and another immune system, called adaptative or specific, which is acquired through cells and mediators of immunity after contact with the potential attacker.

A difference between natural or adaptative immune responses may be found in the identification mechanisms for said microorganisms. With natural immunity, the specificity of receptors is genetically determined since birth and is invariable. These receptors are expressed in cells such as some epithelium and endothelium cells, dendrite cells, monocytes and macrophages. All structures which are identified by natural immunity receptors are common to very many microorganisms. Contrary to the adaptative immune response, the natural immune response mechanisms (phagocytosis, antimicrobial peptides, &c) are activated as early as the beginning of an infection, and they control almost immediately the proliferation of pathogens which invade the host. The adaptative immune response then takes over.

Antimicrobial peptides have been found both in the vegetable and animal kingdoms, and over 500 different antimicrobial peptides have been discovered, from insects to man. Antimicrobial peptides are small molecules (10-50 amino acids), and are able to destroy a great variety of microorganisms (Gram+ or Gram− bacteria, fungi, viruses, transformed cells), by permeabilizing their cell membranes. Moreover some of these antimicrobial peptides are able through chemoattractive properties to recruit cells which participate in adaptative immunity such as dendrite cells or T lymphocytes. Many antimicrobial peptides have been detected in the vernix caseosa and in the amniotic fluid, as well as in newborn infants' skins, which suggests a key role in antimicrobial defence at the time of delivery, but also in the beginnings of life at a time when acquired immunity is still immature.

Most organisms synthesize several types of antimicrobial peptides in their various epithelia, in order to define a wide spectrum of activity. In mammals two main classes of antimicrobial peptides, whose production is induced during contact with a microorganism have been described: cathelicidins and defensins.

Human cathelicidin (LL-37) has been isolated for the first time from bone marrow cells. LL-37 is notably expressed in the human skin, in the region of the nails, as well as in that of the healthy and inflamed synovial membrane, especially with arthrosis patients. LL-37 has a wide spectrum of activity and seems to act synergistically with other antimicrobial peptides, notably defensins. LL-37 also has chemo-attracting properties, which makes it able to recruit adaptative immune cells.

Defensins are themselves divided into two families, or α and β, based on their secondary structure. A-defensins (6 are known to date) are mainly situated in the storage granules of specialized cells, such as neutrophils, or intestine Paneth cells, whereas β-defensins are a characteristic feature of epithelial tissues. Apart from their role in natural immunity, defensins are also known for their mitogenic properties, which suggests they might play a part in the healing processes.

In man 4 β-defensins have been identified to date (over 20 genes coding for antimicrobial peptides seem to exist in our genome). Human β-defensin1 (hBD-1)is generally produced in a constitutive manner, and is abundantly expressed in the kidney, and, to a lesser extent, in the pancreas, salivary glands, airway epithelia, in woman's urogenital system, in the healthy synovial membrane, as well as in the placenta. hBD-1 is also expressed in the skin. Other forms of β-defensins, hBD-2, 3 and 4, are inductible. hBD-3 is induced in the inflamed synovial membranes, such as for instance in arthrotic diseases. The expression of hBD-2 has to date been documented in the skin, the urogenital tract, the sweat glands, and the pilosebaceous unit.

In the skin other peptides or proteins, such as adrenomedullin, cystatin, the specific inhibitor of elastase/SKALP/elafin, would seem to possess antimicrobial activities. More recently dermicidine (with a wide spectrum of activity) has been characterized as an antimicrobial peptide which is specific to the skin, which would seem to be produced in the eccrine sweat glands, and whose secretion, together with sweat, would seem to make up an important part of the natural defence system against local and systemic infections. hBD-2 has been characterized for the first time in psoriasis scales. The expression of hBD-2, as well as of LL-37, is increased in psoriasis lesions, which would explain the greater resistance to infection of patients with this pathology. Conversely in atopic dermatitis (chronic lesions and budding lesions) the expression of LL-37 and hBD-2 decreases under the influence of interleukin-4 (IL-4) and interleukin-13 (IL-13), which are mediators of atopy. This insufficiency could explain the increased sensitivity to infection of patients with atopic dermatitis. In acne the expression of β-defensins (hBD-1 and 2) is increased as a reaction to the proliferation of P acnes. Moreover it is supposed that acneic patients would suffer from an initial imbalance in antimicrobial peptides, which would be responsible for bacterial proliferation. In their turn these bacteria would stimulate natural immune defenses.

Inflammation thus seems to be a primary factor in the induction of antimicrobial peptides. Thus it has also been shown that interleukin-1, TNF-α (Tumor Necrosis Factor alpha) and ultraviolet irradiation would stimulate the production of hBD-2. The expression of hBD-2 is also linked to the differentiation stage of keratinocytes. Thus stimulating the production of antimicrobial peptides, notably within the defensin family, and more particularly of hBD-2, would make it possible to enhance and/or to restore natural immunity, especially in the eye and the epithelia (epidermis, vaginal, intestinal, nasal and auricular mucosae, and airways).

The buccal cavity is constantly open to a great variety of microorganisms (bacteria, viruses, fungi). Among other facts, it is well established that bacteria such as *Actinobacillus* actinomycetemcomitans, *Porphyromonas gingivalis*, are key factors participating in the development of periodontal diseases (gingivitis and parodontitis). The gingival epithelium is the first bastion against the various pathogens which may be found in the region of the mouth. As such gingival keratinocytes yield a wide panel of antimicrobial peptides, hBD-1, -2, -3, LL-37. These peptides are also produced in the buccal mucosa, as well as by salivary glands.

More particularly the stimulation of antimicrobial peptides would make it possible to enhance and/or to restore natural immunity in the healthy or diseased skin of newborn infants and children, whose immunity is generally deficient, and in the skin of adults or aged persons, whether in good health or not (immunodepressed). This stimulation would thus make it possible to advantageously supplement the skin's passive defence system as made up by the stratum corneum (corneocytes+intercellular cement), and to prepare the adaptive immune response in newborn infants, children, adults and aged persons, whether in good health or not. In the same manner, this stimulation would make it possible to accelerate healing.

In a surprising manner the inventors have discovered that a composition comprising an avocado peptide extract makes it possible to increase the production of antimicrobial peptides, advantageously of hBD-2.

Thus the aim of the invention is a drug comprising an avocado peptide extract, which includes 2-10 weight % alpha-aminated nitrogen, in relation to the dry matter weight of the peptide extract, and an appropriate excipient.

In this invention the phrase 'alpha-aminated nitrogen' means the nitrogen content of peptides in the form of free alpha-aminated groups. A measurement of the alpha-aminated nitrogen content of peptides allows one to evaluate the hydrolysis level of proteins as well as the average molecular weight of peptides.

The avocado peptide extract may be directly obtained from any part of the avocado or avocado tree, such as the fruit, the skin, the stone, the leaf or the roots of the tree. One may also obtain an avocado peptide extract from by-products of the avocado processing industry, of which may be cited, among others: the fresh avocado pulp, the quick frozen or dehydrated pulp, avocado cakes from oil extracting processes (mechanical and/or solvent extraction of the previously dehydrated fruit), de-oiled solid matter from wet oil extracting processes (so-called centrifugation process), de-oiled solid matter from enzymatic avocado oil extracting processes, raw mashed avocado (guacamole), solid refuse from plants manufacturing these mashed products. The extract is advantageously obtained from the fresh avocado tree fruit. Fruits may be chosen among the Hass, Fuerte, Ettinger, Bacon, Nabal, Anaheim, Lula, Reed, Zutano, Queen, Criola Selva, Mexicana Canta, Region Dschang, Hall, Booth, Peterson and Collinson Red varieties, more advantageously the Hass, Fuerte and Red varieties. Preferably the Hass, Fuerte, Ettinger and Bacon varieties will be retained, and most preferably the Hass and Fuerte varieties.

The avocado tree fruit is principally made up of water, pulp, oil and a stone. The proportions of these various constituents are extremely variable, as is the case with all natural products. However one may generally assume the following average composition, as expressed in percentage of the fresh fruit, and shown in the following Table 1:

TABLE 1

| | |
|---|---|
| Water | 70-85% |
| Proteins | 1.5-4.5% |
| Lipids | 12-23% |
| Sugars | 1.5-5% |
| Fibers | 1.1-1.6% |

In relation to the pulp, the avocado proteins represent 1.5-2.5% (J. P. Gaillard, l'Avocatier, Edition G. P. Maisonneuve et Larose, 1987, pages 266-67). The distribution of amino acids, as expressed in weight percentage in relation to the total weight of amino acids, is shown in the following Table 2:

TABLE 2

| | |
|---|---|
| Alanine | 5-7 |
| Arginine | 3-5 |
| Aspartic acid | 8-12 |
| Cystine-Cysteine | <1 |
| Glutamic acid | 11-13 |
| Glycine | 4-6 |
| Histidine | 4-6 |
| Isoleucine | 4-7 |
| Leucine | 8-11 |
| Lysine | 4-7 |
| Methionine | 1-3 |
| Phenylalanine | 4-6 |
| Proline | 4-7 |
| Serine | 4-6 |
| Threonine | 4-6 |
| Tyrosine | 3-6 |
| Valine | 4-7 |

The main amino acids are glutamic acid, aspartic acid and leucine.

As compared with conventional oleoproteaceous plants such as soy bean, sunflower or rapeseed, the avocado is distinctly lower in protein content. Moreover, the fruit having a comparatively high fiber content, these proteins are made highly inaccessible through conventional chemical or biochemical paths. What is more, these natural macromolecules being hardly hydrosoluble, one tends to prepare hydrolyzed fractions of these proteins (peptides), which are highly watersoluble and more easily bioavailable. Thus their allergenic power may also be eliminated. Therefore the invention also concerns the preparation of an avocado peptide extract via a gentle synthesis path which does not denaturate hydrolyzed proteins.

More particularly the avocado peptide extract may be obtained by a process comprising the following steps:
  an avocado cake is obtained, advantageously from avocado fruit, through drying and extraction of the oil (lipids); after which
  said cake is ground in the cold (cryogrinding) and totally delipidated, then allowed to settle, centrifuged and collected; after which
  a first hydrolysis is carried out in the presence of glucanases, this being followed by a centrifugation process and the elimination of the soluble fraction;
  a second hydrolysis is carried out in the presence of one or more proteases, this being followed by a centrifugation process and the elimination of the residue; after which
  the peptide phase is concentrated by nanofiltration;
  a discoloration is carried out in the presence of activated carbon, for instance, this being followed by a simple filtration (10 µm), then by an ultrafiltration (cutting limit 10 kD); and finally
  if need be, a final sterilizing microfiltration (0.2 µm), with preservative added and a packaging operation are carried out.

According to an advantageous variant of the invention, the first step of the process consists in drying, then deoiling the fruit. Thus after the fruit has been cut into thin slices it may be dried by any one of the set of techniques known to art specialists, among which may be cited hot air drying, freeze-drying or osmotic drying. Temperature during this drying step will generally be advantageously maintained below or at 80° C., whatever the technique which is used. Within this process, for reasons of easy implementation and cost, drying in ventilated dryers, in thin layer and under a hot air flow at a temperature between 70-75° C. is preferred. This operation may last between 5 and 72 hours.

Lipids in the dried fruit are later extracted either mechanically in a worm screw press, or chemically with a solvent such as hexane in a Soxhlet type extractor or in a De Smet® type continuous band extractor, notably according to the process as described in French application FR 2 843 027, or by a process using supercritical $CO_2$. Among the main benefits of this process the oil by-product is a substance which may naturally be directly recycled. For this reason mechanical lipid extraction is preferred.

The dried and deoiled fruit, also called a cake, may then be subjected to the following steps:
- cryogrinding,
- total delipidation, notably with a non toxic food grade solvent such as ethanol and/or acetone,
- decanting and washing of the cake with water,
- centrifugation and collection of the cake,
- a first hydrolysis in the presence of one or several glucanases,
- centrifugation and discarding of the soluble fraction,
- a second hydrolysis in the presence of one or several proteases,
- centrifugation and discarding of the residue,
- concentration through nanofiltration,
- discoloration in the presence of activated carbon,
- a simple filtration (10 μm) followed by an ultrafiltration (cutting limit 10 kD),
- addition of a preservative, final sterilizing microfiltration (0.2 μm) and packaging.

The final aqueous extract may contain 1-60 weight % dry matter, or 3-20% dry matter, preferably 5-6% dry matter. In relation to the dry matter weight, the mass content of alpha-aminated nitrogen may be between 2-10%, preferably between 5-7%. The pH value of a 1.2 weight % dry extract aqueous solution will generally be between 3-6, more advantageously between 4-5. Mean analytic data for a 1.2 weight % dry extract aqueous solution, as obtained by the above described process, are shown in the following Table 3:

TABLE 3

| | |
|---|---|
| Alpha-aminated nitrogen (called 'o-phtalaldehyde' or 'ninhydrine' method) (as a mass % in dry matter) | 4-10 |
| Proteins (as a mass % in dry matter) (N × 6.25)[1] | 10-30 |
| pH value (¼ dilution) | 4.5-7.0 |
| Absorbance (¼ dilution) 420 nm | 0.1-0.6 |
| Absorbance (¼ dilution) 550 nm | 0.02-0.1 |

[1] N × 6.25 corresponds to a total nitrogen (N) dosage of a sample, multiplied by a coefficient which is specific for the assayed protein. When the coefficient for assayed proteins is not known with precision, a coefficient of 6.25 is conventionally used.

The following Table 4 shows the average amino acid composition of the peptide extract as obtained by the inventive process, in which the values are expressed in weight % in relation to the total weight of assayed amino acids.

Values for aspartic acid and glutamic acid also include asparagine and glutamine contents, respectively.

TABLE 4

| Amino acid | Minimum value | Maximum value |
|---|---|---|
| Alanine | 6.4 | 7.8 |
| Arginine | 4.7 | 5.7 |
| Aspartic acid | 10.3 | 12.7 |
| Cystine-Cysteine | 2.9 | 3.5 |
| Glutamic acid | 13.0 | 15.8 |
| Glycine | 5.3 | 6.5 |
| Histidine | 2.2 | 2.6 |
| Isoleucine | 4.8 | 5.8 |
| Leucine | 7.6 | 9.4 |
| Lysine | 3.0 | 3.8 |
| Methionine | 1.2 | 1.6 |
| Phenylalanine | 4.7 | 5.7 |
| Proline | 4.1 | 5.2 |
| Serine | 5.5 | 6.7 |
| Threonine | 4.6 | 5.6 |
| Tyrosine | 3.6 | 4.4 |
| Valine | 5.8 | 7.2 |

Tryptophan not Assayed

The obtained extract may be freeze-dried in order to obtain a solid powder (dry extract), but it is totally hydrosoluble in relation to the original avocado proteins.

According to an advantageous variant of the invention, at least 50% of the extract peptides are made up of 10-30 amino acid sequences. The size of these peptides is therefore much smaller as compared with that of the avocado's native proteins. Therefore these peptides thus possess a much better bioavailability, notably on the skin.

The drug of the invention is particularly appropriate for the treatment and/or the prevention of diseases which are linked to a change in natural and/or acquired immunity, through an increase in the production of antimicrobial peptides, belonging to the cathelicidin and/or beta-defensin families, advantageously hBD-2. In the sense of this invention, a 'change' may mean an increase or a decrease.

The drug of the invention is also particularly appropriate for the treatment and/or prevention of diseases as linked to a change in natural and/or acquired immunity through stimulation of antimicrobial peptides like a specific elastase inhibitor, particularly elafin (SKALP).

The drug of the invention makes it possible to advantageously stimulate and/or supplement natural and/or acquired immunity.

Within the scope of the invention, said diseases may generally be linked to the presence of microorganisms, notably Gram+ and/or Gram− bacteria, fungi or viruses.

More particularly said diseases may be infections of the organs of sight and audition, non keratinized epithelia (vaginal, intestinal, gingival, nasal, pulmonary, respiratory tract, anal and urethral mucosae) and keratinized epithemia such as the skin. Said diseases may also be infections of the teguments or skin phanerae (hair, nails, sweat glands, sebaceous glands). Thus said diseases may be pathologies such as folliculitis, furuncles, abscess, impetigo or whitlow.

Said diseases may be pathologies of the scalp such as dandruffs and in a wider sense conditions linked to a hyperseborrhoea.

Said diseases may be pathologies which are linked to a change in the Th1/Th2 balance, such as atopic dermatitis.

Said diseases may be pathologies which are linked to changes in the synthesis of cytokins, such as IL-4 and/or IL-13, notably within the frame of atopic dermatitis.

Said diseases may also be inflammatory dermatoses, such as atopic dermatitis, atopic eczema and/or contact dermatitis, psoriasis, acne and itching dermatites.

Said diseases may also be burns, particularly first or second grade burns.

Said diseases may also be pathologies which are linked to a deficiency in the skin barrier. Thus the inventive drug may be used for the treatment of hyperreactive skins (sensitive, irritated, allergic), atopic, dry or aged skins. Said diseases may also be pathologies which are linked to skins made vulnerable by aggression from the environment, notably due to cold, pollution, stress, tobacco or sun exposure.

Within the scope of this invention, the drug is also appropriate for the protection of immature, healthy or pathological skins in newborn infants and children. Indeed it allows one to reinforce the natural defences of a child's epidermis when immunity is generally deficient.

Within the scope of this invention the drug is also appropriate for the protection of healthy or pathological skins in adults or in the elderly, notably with immunodepressed persons.

The inventive drug is also appropriate for enhancing the healing process, whether normal or pathological, such as ulcers or bedsores.

Within the scope of this invention the drug is also aimed for the treatment and/or prevention of periodontal diseases, inflammatory articular pathologies such as arthrosis, infections of the mucosae, notably the vaginal, intestinal, respiratory, nasal or auricular mucosae, or the infections of the sight organs.

According to an advantageous variant of the invention the drug comprises 0.1.-20 dry weight % avocado peptide extract, in relation to the total weight of said drug, more advantageously 0.1-15 dry weight % avocado peptide extract, more advantageously still 0.5-10 dry weight % avocado peptide extract, more advantageously still 0.7-8 dry weight % avocado peptide extract, and more advantageously still 1-5 dry weight % avocado peptide extract.

According to an advantageous variant of the invention the drug moreover comprises D-mannoheptulose and/or perseitol (C7 sugars) or one of their chemical derivatives, advantageously in an amount of 0.001-30 dry weight %, in relation to the total weight of the drug, more advantageously 0.01-20 dry weight %, more advantageously still 0.1-10 dry weight %, more advantageously still 0.5-5 dry weight %.

A synergistic effect is then advantageously observed.

The D-mannoheptulose and/or perseitol source is advantageously either a hydrosoluble sugar extract from avocado or other plants. Otherwise D-mannoheptulose and perseitol are commonly marketed (synthetic origin).

According to an advantageous variant of the invention the D-mannoheptulose and/or perseitol source is an avocado sugar hydrosoluble extract comprising at least 50 weight % C7 sugars, in relation to the total weight of the extract dry matter.

The avocado sugars hydrosoluble extract may be obtained by a process which comprises the following sequence of steps:
  obtaining an avocado cake, advantageously from avocado fruit, by drying the avocado and extracting the lipids (oil); followed by
  cryogrinding and total delipidation of said cake, then settling and centrifugation in order to collect a soluble fraction having a high C7 sugars content (discarding of the cake);
  demineralization on an ionic resin of said soluble fraction as obtained in the preceding step; followed by
  an ultrafiltration at 10,000 Daltons;
  if need be, concentration by vacuum vaporising, addition of a preservative, sterilization by microfiltration (0.2 μm) and packaging.

According to a preferred variant of the invention, the processes whereby the avocado cake is obtained and the lipids are extracted are advantageously carried out in an identical manner for the avocado peptide extract and the avocado sugars.

The dried and deoiled fruit, also called cake, may then be subjected to the following steps:
  cryogrinding,
  total delipidation, advantageously with ethanol and/or acetone,
  settling and washing the cake with water,
  centrifugation and collection of the soluble fraction (discarding of the cake),
  demineralization by passing over ion exchange resins
  ultrafiltration with a cut-off limit of 10 kD,
  vacuum concentration, addition of a preservative and packaging.

The final aqueous extract may generally contain 0.1-10 weight % dry matter, advantageously 1-7 weight % dry matter, more advantageously 3-5% dry matter. The C7 sugar, that is D-mannoheptulose and perseitol content in the dry matter is advantageously above 50 weight %, more advantageously between 65-90 weight %, in relation to the total dry matter weight.

The relative sugar composition of the avocado hydrosoluble extract, as expressed in weight in relation to the total weight of the extract dry matter, advantageously fills the following criteria (relative composition as determined by HPLC):

| | |
|---|---|
| D-mannoheptulose | 5-80% |
| Perseitol | 5-80% |
| Sucrose | <10% |
| Glucose | <10% |
| Fructose | <10% |

The avocado sugar hydrosoluble extract advantageously comprises, in relation to the total dry matter weight, 1-99 weight % mannoheptulose, more advantageously 5-80 weight % mannoheptulose, more advantageously still 10-80 weight % mannoheptulose. The avocado sugar hydrosoluble extract advantageously comprises, in relation to the total dry matter weight, 20-80 weight % perseitol, more advantageously 25-70 weight % perseitol.

Preferably the relative sugar composition of the hydrosoluble extract, as expressed in weight in relation to the total extract dry matter weight, fills the following criteria (relative composition as determined by HPLC):

| | |
|---|---|
| D-mannoheptulose | 25-60% |
| Perseitol | 25-60% |
| Sucrose | <10% |
| Glucose | <10% |
| Fructose | <10% |

If need be the obtained extract may be freeze-dried in order to obtain a solid powder (dry extract) which is totally hydrosoluble.

According to an advantageous variant of the invention, the inventive drug moreover comprises a lupine peptide extract, advantageously in a mass amount, in relation to the total drug weight, between 0.001-30 dry weight %, more advantageously still between 0.01-10 dry weight %. The lupine peptide extract, as added into the inventive composition, comprises at least 70 weight % peptides, advantageously at least 80 weight %, in relation to the dry matter weight of the peptide extract. A synergistic effect is then advantageously observed.

Particularly the lupine peptide extract may be obtained by a process which comprises the following steps:
- preparation of a ground lupine cake or a micronized lupine flour cake;
- followed by delipidation through solvent extraction;
- extraction of soluble protein and osidic fractions, or precipitation of proteins at the isoelectric point;
- if need be, separation of the protein fraction;
- enzyme hydrolysis of the protein fraction, and collection, possibly after filtration, of the peptide extract.

A process for preparing a peptide extract is described in French patent publication FR 2 792 202, filed by Expanscience Laboratories.

The drug of the invention may moreover comprise at least one compound as chosen within the group made up by emollients, moisturizing active substances, activators of keratin synthesis, keratoregulators, keratolytics, restructuring agents for the skin barrier (skin lipid synthesis activators, PPARs or Peroxysome Proliferator Activated Receptors agonists), activators in the differentiation of keratinocytes (retinoids, Calcidone®, calcium), antibiotics, antibacterial agents, antifungic agents, antiviral agents, seboregulators, such as 5-alpha reductase inhibitors, notably the active substance 5-alpha Avocuta®, as marketed by Expanscience Laboratories, immunomodulators, such as tacrolimus, pimecrolimus, oxazolines, preservatives, anti-itching agents, soothing agents, filters and sunscreens, anti-oxidant agents, growth factors, healing agents or eutrophic molecules, anti-inflammatory drugs and agents, and compounds containing vegetable oil insaponifiables.

The keratin synthesis activators which may be used within the scope of this invention in association with the avocado peptide extract, are advantageously retinoids, lupine peptides (as marketed by the Silab Company), key proteins of the stratum corneum or granulosum (keratins).

Antibiotics which may be used within the scope of this invention, in association with the avocado peptide extract, are advantageously fucidic acid, penicillin, tetracyclines, pristamycin, erythromycin, clindamycin, mupirocin, minocycline, and doxycycline. Antiviral agents which may be used within the scope of this invention, in association with the avocado peptide extract, are advantageously acyclovir and valacyclovir. Anti-itching agents which may be used within the scope of this invention, in association with the avocado peptide extract, are advantageously glycine, lupine sugars and/or peptides, Cycloceramide®.

Soothing agents which may be used within the scope of this invention, in association with the avocado peptide extract, are advantageously alpha bisabolol, liquorice derivatives. Keratoregulators which may be used within the scope of this invention, in association with the avocado peptide extract, are advantageously alpha hydroxy acids and their derivatives. A keratolytic substance which may be used within the scope of this invention, in association with the avocado peptide extract, is notably salicylic acid and its derivatives. Anti-oxidant agents which may be used within the scope of this invention, in association with the avocado peptide extract, are advantageously vitamins (C, E), trace elements (copper, zinc, selenium). Growth factors which may be used within the scope of this invention, in association with the avocado peptide extract, are advantageously becaplermine and TGF beta (Transforming Growth Factor beta).

Healing agents which may be used within the scope of this invention, in association with the avocado peptide extract, are advantageously vitamin A, panthenol, Avocadofurane®, zinc oxide, magnesium, madecassic or Asiatic acid.

Drugs which may be used within the scope of this invention, in association with the avocado peptide extract, are advantageously drugs which are appropriately delivered topically or orally, for the prevention and/or treatment of atopy (corticoids, emollients), acne (antibiotics, benzoyl peroxide, retinoids, azelaic acid, vitamin PP, zinc, cyclines), of eczema (immunomodulators, emollients, salmon oil, borage oil, prebiotics) or of psoriasis (corticoids, calcipotriol, calcitriol, tazarotene, cade oil, acitretin, PUVA therapy).

Anti-inflammatory agents which may be used within the scope of this invention, in association with the avocado peptide extract, are advantageously steroidal anti-inflammatory agents (AIS), such as corticoids, or non steroidal agents (AINS). Restructuring agents of the skin barrier, which make it possible to stimulate the synthesis of key lipids in the epidermis, and which may be used within the scope of this invention, in association—advantageously with a synergistic effect—with the avocado peptide extract, are advantageously sunflower concentrates, more advantageously linoleic sunflower concentrates, such as the active substance as marketed by Expanscience Laboratories, Soline® (see International Application WO 01/21150), vegetable oil insaponifiables, such as Avocadofurane® (see International Application WO 01/21150), PPARs agonists (rosiglitazone, pioglitazone). Restructuring agents are advantageously present in proportions between 0.001 and 30 weight %, in relation to the total weight of the drug. Antifungal compounds which may be used within the scope of this invention, in association with the avocado peptide extract, are advantageously econazole and ketoconazole.

Antiseptic preservatives which may be used within the scope of this invention, in association with the avocado peptide extract, are for instance triclosan, chlorhexidine, quaternary ammonia.

Immunomodulators which may be used within the scope of this invention, in association with the avocado peptide extract, are advantageously tacrolimus, pimecrolimus and oxazolines.

Oxazolines which may be used within the scope of this invention, in association—advantageously with a synergistic effect—with the avocado peptide extract, are advantageously oxazolines which are chosen among the group made up by 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline. In a still more advantageous manner, said oxazoline is 2-undecyl-4,4-dimethyl-1,3-oxazoline, called OX-100 or Cycloceramide®.

The compounds which contain vegetable oil insaponifiables, and which may be used within the scope of this invention, in association, advantageously with a synergistic effect, with the avocado peptide extract, are preferably chosen within the group made up by avocado furane lipids, avocado and soy bean insaponifiables, lupine oil concentrates, sunflower oil concentrates, and their mixtures.

The avocado furane lipids which may be used within the scope of this invention, in association, advantageously with a synergistic effect, with the avocado peptide extract, are preferably natural 2-alkyl furanes, notably the active substance Avocadofurane® as marketed by Expanscience Laboratories, which may be obtained by the process as described in International Application WO 01/21605.

Avocado and soy bean insaponifiables which may be used within the framework of this invention, in association, advantageously with a synergistic effect, with the avocado peptide extract, are preferably a mixture of furane avocado insaponifiables and soy bean insaponifiables, in a respective ratio of about 1/3-2/3. Avocado and soy bean insaponifiables are more advantageously the product Piasclédine®, as marketed by Expanscience Laboratories.

Lupine oil concentrates which may be used within the scope of this invention, in association, advantageously with a synergistic effect, with the avocado peptide extract, are advantageously concentrates which are obtained through molecular distillation of lupine oil, advantageously sweet white lupine oil, such as those described in International Application WO 98/47479. They contain, advantageously, some 60 weight % insaponifiables.

The sunflower oil concentrates which may be used within the scope of this invention, in association, advantageously with a synergistic effect, with the avocado peptide extract, are advantageously linoleic sunflower concentrates, such as the active substance marketed by Expanscience Laboratories, Soline® (see International Application WO 01/21150).

The drug of the invention is aimed at the treatment and/or prevention of diseases which may affect man and/or animals, notably mammals. The drug of the invention may be formulated in the form of various preparations which are adapted for topical administration, for oral, rectal, vaginal, nasal, auricular or bronchial administration, for parenteral administration. Preferably the various preparations are adapted for topical administration and include creams, ointments, lotions, oils, patches, sprays, or any other product for external application. Routes for administrating the inventive compounds and compositions, optimal dosage and drug forms may be determined following criteria which are generally taken into account in establishing a pharmaceutical treatment, particularly in the fields of dermatology or veterinary medicine, as adapted to a patient or an animal, such as, for instance, the age or body weight of the patient or animal, the seriousness of his/its condition, tolerance towards the particular treatment, the side effects observed, and the type of skin. According to the type of administration which is sought, the inventive drug and/or active substances may moreover comprise at least one pharmaceutically suitable, notably dermatologically suitable, excipient. One may preferably use an excipient which is adapted for topical external administration. The inventive drug may moreover comprise at least one pharmaceutically known additive, as pharmaceutically known to art specialists, chosen among thickeners, preservatives, perfumes, colouring agents, chemical filters or minerals, moisturizing agents, thermal waters, etc.

This invention also relates to a cosmetic composition comprising an avocado peptide extract and a cosmetically suitable appropriate excipient. The avocado peptide extract advantageously comprises 2-10 weight % alpha-aminated nitrogen, in relation to the dry matter weight of the peptide extract.

The inventive cosmetic composition advantageously comprises 0.001-30 dry weight % avocado peptide extract, in relation to the total weight of said composition, more advantageously still 0.01-10 dry weight % avocado peptide extract. According to a preferred version of the invention the avocado peptide extract may be obtained according to a process such as previously described.

According to an advantageous version of the invention, the composition moreover comprises D-mannoheptulose and/or perseitol (synergistic effect), advantageously in an amount of 0.001-30 dry weight %, more advantageously still 0.01-5 dry weight %, in relation to the total weight of the composition. The D-mannoheptulose and/or perseitol source is advantageously a hydrosoluble avocado sugars extract whose C7 sugar content—that is to say the D-mannoheptulose and perseitol content—in the dry matter is advantageously between 65-90 weight %, in relation to the total dry matter weight. These heptitol type sugars may also be obtained from another vegetable source or by synthesis.

According to an advantageous variant of the invention, the composition moreover comprises a lupine peptide extract (synergistic effect), advantageously in an amount of 0.001-30 weight %, in relation to the total weight of the composition. The lupine peptide extract, as added into the inventive composition, comprises at least 70 weight %, advantageously at least 80% peptides, in relation to the dry matter weight of the peptide extract. It may be obtained according to a process such as hereabove described.

The composition may moreover contain at least one compound chosen among the group made up by the skin barrier's restructuring agents and compounds containing vegetable oil insaponifiables, such as hereabove defined. In particular the cosmetic composition may contain an active substance chosen among the group made up by Saline®, Avocadofurane® and Piasclédine®, as marketed by Expanscience Laboratories.

The inventive cosmetic composition comprises advantageously 0.001-30 weight %, in relation to the total weight of the composition, of at least one skin barrier restructuring agent.

The inventive cosmetic composition may be formulated in the form of various preparations adapted for topical administration, oral, rectal or vaginal administration, or parenteral administration. Preferably the various preparations are adapted for topical administration and include creams, ointments, lotions, oils, patches, sprays or any other products for external application. According to the type of administration which is aimed at, the inventive composition and/or active compounds may moreover comprise at least one cosmetically suitable excipient. The inventive cosmetic composition may moreover comprise at least one additive which is known to the art specialist, and chosen among thickeners, preservatives, perfumes, colouring agents, chemical fibers or minerals, moisturizing agents, thermal waters, etc.

This invention also relates to a process for the cosmetic treatment of sensitive, irritated, intolerant skins and/or mucosae, which present cutaneous reddenings, or a non pathological immunological imbalance, characterized in that it implies applying onto the skin and/or the mucosae an inventive cosmetic composition.

This invention finally relates to a nutraceutic composition comprising an avocado peptide extract, and, if need be, a suitable appropriate excipient. The avocado peptide extract advantageously comprises 2-10 weight % alpha-aminated nitrogen, in relation to the dry matter weight of the peptide extract.

The inventive neutraceutic composition advantageously comprises 0.001-30 weight % avocado peptide extract, in relation to the total weight of said composition, more advantageously 0.01-10 weight % avocado peptide extract. According to an advantageous variant of the invention, the avocado peptide extract may be obtained according to a process such as hereabove described.

According to an advantageous variant of the invention, the nutraceutic composition also comprises D-mannoheptulose and/or perseitol (synergistic effect), advantageously in an amount of 0.001-30 dry weight %, in relation to the total weight of the composition. The D-mannoheptuolse and/or perseitol source is advantageously an avocado sugar hydrosoluble extract, whose C7 sugar content, that is to say the D-mannoheptulose and perseitol content in the dry matter is advantageously between 65-90 weight %, in relation to the total dry matter weight.

According to an advantageous variant of the invention, the nutraceutic composition comprises at least a lupine peptide extract (synergistic effect), advantageously in an amount of 0.001-30 dry weight %, in relation to the total weight of the composition. The lupine peptide extract, as added into the inventive composition, comprises at least 70 weight %, advantageously at least 80% peptides, in relation to the peptide extract dry matter weight. It may be obtained according to a process such as hereabove described.

The following non limitative Examples illustrate the invention.

Example 1

Preparation of an Avocado Peptide Extract 50 kg fresh avocado, Hass variety, are cut into thin slices, 2-5 mm thick, stone included, with a disk cutting machine. The drying apparatus is a hot air flow thermoregulated oven. Once cut the avocados are distributed into 4-5 cm thick layers onto trays which are laid out in tiers. Drying temperature is set at 80° C. for a total duration of 48 hours. Once dried the fruit are exposed to cold pressure. This operation is carried out on a small Komet® laboratory press.

The 4 kg delipidated pieces of fruit (cake) are then broke at a cold temperature, then extracted with reflux, in the presence of 25 liters of ethanol. The powder, with the lipids exhausted, is then collected by filtration onto a Büchner funnel, and dried in the oven at 50° C. during 5 hours.

The cake is then washed with demineralised water (10 l), then separated by centrifugation. The solid fraction is taken up in an aqueous solution, acidified with HCl (with a pH value set at 5), then brought in the presence of 2% cellulase (in relation to dry matter). Duration of the hydrolysis is set at 6 hours.

The mixture is then centrifuged at 2,000 g in the presence of an additive (2.5% p/v). The residue which is collected is then subjected to a second hydrolysis at a pH value of 8.0, in the presence of 0.5% protease, at a temperature of 55° C., during 2 hours. Hydrolysis is regulated at a constant pH value by the continuous addition of 2 M sodium hydroxide. The protease is finally denatured by heating during 10 minutes at 85° C.

The mixture as obtained is centrifuged and the supernatant is filtrated by passing through a 7.5 μm membrane. It is then ultrafiltrated on membranes having a 10 kD cutoff limit.

The raw peptide extract as obtained with 20% dry matter is discoloured in the presence of 1% activated carbon, then again filtrated through a 7.5 μm membrane. The discoloured extract is then microfiltrated (0.2 μm), its titter is adjusted to 5% dry matter, and then it is supplemented with a preservative and finally packaged after a sterilizing filtration (0.2 μm).

Characteristic data of the hydrosoluble avocado peptide extract (5% dry matter) as obtained by this process are shown in the following Table 5:

TABLE 5

| Appearance | Slightly orange-colored solution |
|---|---|
| Analytic criteria | |
| Dry matter | 5% |
| pH value (¼ dilution) | 14.5 |
| Absorbance at 420 nm (¼ dilution) | 0.152 |
| Absorbance at 550 nm (¼ dilution) | 0.035 |
| Dry matter composition | |
| Alpha-aminated nitrogen | 6.7% |
| Proteins | Not detected |
| Preservative | 0.4% |

In the following Table 6, the molecular mass distribution in the avocado peptide extract as obtained by this process is given:

| HPLC peak | Molecular mass (g/mol) | Average number of amino acids | Relative % |
|---|---|---|---|
| 1 | >3480 (1) | <29 | 1% |
| 2 | 3480-1180 | 29-9 | 26% |
| 3 | 1180-310 | 9-2 | 45% |
| 4 | 310-130 | 2-1 | 15% |
| 5 | <130 | 1 | 13% |

(1) mass < 10000 g/mol

It may be observed that at least 27% of peptides in the extract are made up of at least 9 amino acid sequences. Therefore the size of peptides in the extract is very small in relation to that of the natural proteins in the avocado. Thus these peptides possess a much higher bioavailability, notably on the skin.

Example 2

Preparation of an Avocado Sugar Hydrosoluble Extract 50 kg fresh avocado, Hass variety, are cut into thin slices, 2-5 mm thick, stone included, with a disk cutting machine. The drying apparatus is a hot air flow thermoregulated oven. Once cut the avocados are distributed into 4-5 cm thick layers onto trays which are laid out in tiers. Drying temperature is set at 80° C. for a total duration of 48 hours. Once dried the fruit are exposed to cold pressure. This operation is carried out on a small Komet® laboratory press.

The 4 kg delipidated pieces of fruit (cake) are then ground at a cold temperature, then extracted with reflux, in the presence of 25 liters of ethanol. The powder, with the lipids exhausted, is then collected by filtration onto a Büchner funnel, and dried in the oven at 50° C. during 5 hours.

The cake is then washed with demineralised water (10 l), then separated by centrifugation. The soluble fraction (liquid) is taken up in order to be purified and concentrated according to the following process:

Demineralization with ion exchange resins: demineralization of heptuloses by passing onto OH⁻, then H⁺ resin.

Ultrafiltration on 10,000 Da: ultrafiltration is carried out using a system which is equipped with 4 membranes having a cutoff limit of 10 kDa.

Vacuum concentration: concentration of the purified extract is carried out with a vacuum evaporator until dry matter at about 4% is obtained.

Packaging: concentration of the extract is adjusted at 5% dry matter and a preservative is added, then a sterile filtration is carried out with a 0.2 μm cutoff limit membrane, and the product is packed.

The following Table 7 shows the composition of the C7 avocado sugar extract, at 5% dry matter, as prepared according to the hereabove described process:

TABLE 7

| Appearance<br>Analytical criteria | Pale yellow coloured solution |
|---|---|
| Dry matter | 5% |
| pH value (¼ dilution) | 7.0 |
| Absorbance at 420 nm (¼ dilution) | 0.013 |
| Absorbance at 550 nm (¼ dilution) | 0.003 |
| Composition (% dry matter) | |
| Sucrose | 3.0 |
| Glucose | 7.5 |
| D-mannoheptulose | 40.0 |
| Fructose | 10.6 |
| Perseitol | 28.8 |

Example 3

Induction of Beta-Defensin-2 with the Avocado Peptide Extract

Cell Seeding (J0):

Normal human keratinocytes are seeded in 96 well plates (about 20,000 cells/well), in the presence of a specific medium which is enriched in calcium (final concentration 1.3 mM), as formerly described in the publication 'Human β-Defensin-2 production in Keratinocytes is regulated by Interleukin-1, Bacteria, and the State of Differentiation', Alice Y. Liu et al., The Society for Investigative Dermatology, vol. 118, No 2, February 2002, pages 275-281.

Cell Processing (J1):

After incubation for 24 hours at 37° C., 5% $CO_2$:
2 rinses with 200 μl/well PBS (phosphate buffer in saline solution)
cell stimulation with 200 μl/well (in medium supplemented with $Ca^{++}$):
avocado peptide extract at concentrations of 3, 1 and 0.3%, or, respectively, 0.15, 0.05 and 0.015% dry matter
Il-1β at a concentration of 100 ng/ml (positive induction checking for hBD-2)

End of Processing (J2): ELISA

After 24 hours incubation, the induction of hBD-2 is assessed with an ELISA technique using a specific antibody (goat polyclonal to human BD2; Abcam; ab9871).

The obtained results are summarised in the following Table 8:

TABLE 8

| | Control cells | Positive control (IL-1β) | Avocado peptide extract (0.3%) | Avocado peptide extract (1%) | Avocado peptide extract (3%) |
|---|---|---|---|---|---|
| hBD-2 (OD) | 0.03 | 0.103 | 0.057 | 0.047 | 0.05 |
| hBD-2 (OD) | 0.036 | 0.11 | 0.056 | 0.056 | 0.063 |
| hBD-2 (OD) | 0.036 | 0.105 | 0.062 | 0.054 | 0.072 |
| Average | 0.034 | 0.106 | 0.058 | 0.052 | 0.062 |

It may be observed that, in a quite unexpected manner, the inventive avocado peptide extract allows one to increase the amount of hBD-2 which is produced.

Example 4

Induction of mRNAs which Code for hBD-2 and for Antimicrobial Like Peptides (Elastase Specific Inhibitor)

The 'cDNA micro array' method was used to study the effects of avocado peptide extracts on the expression of genes which code for structural and regulatory proteins which might be of interest in skin physiology. Such an approach allows one to screen in a single step the effects of a product or of a treatment on the expression of genes in a given biological system, and to obtain a 'signature' of the effects of this treatment.

Conditions of Culture and Assayed Products

The avocado peptide extracts, at concentrations of 3, 1 and 0.3%, or, respectively, 0.15, 0.05 and 0.015% dry matter, as obtained by the inventive process, were directly incubated in the culture medium for reconstructed epidermis, Skinethic®, during 24 hours.

Analysis of Gene Differential Expression

The approach used, which is recommended by Clontech (Palo Alto, USA), comprises:
- A total RNA extraction and purification step
- A messenger RNA purification step according to the AtlasPure protocol (Clontech)
- A labelling of DNA probes with $P^{32}$ using reverse transcription
- A purification of probes as labelled by exclusion column chromatography, and checking of the quality and equivalence by liquid scintillation counting.
- A hybridation of membranes (Custom ATLAS BIOAlternative) with the radiolabelled probes (68° C., overnight).

Results

The effects on the synthesis of mRNAs coding for antimicrobial peptides (hBD-2) and antimicrobial like peptides (Elastase specific inhibitor/SKALP/elafin) are shown in the following Table 9:

TABLE 9

| GENES | Avocado peptide extract, pure active (0.015%) | Avocado peptide extract, pure active (0.05%) | Avocado peptide extract, pure active (0.15%) |
|---|---|---|---|
| Beta defensin 2 | 16.1 | 69.7 | 103.9 |
| Specific Elastase Inhibitor | 5.5 | 14.7 | 13.5 |

Example 5

Cosmetic Formulations Based on Avocado Peptide Extract

Anti-acneic Cream No 1

| Water | QSP 100% |
|---|---|
| Isononyl Isononanoate | 7.000 |
| Di-$C_{12-13}$ malate | 7.000 |
| Isocetyl stearate | 5.000 |
| Butytlene glycol | 3.000 |
| *Oryza sativa* | 2.500 |
| Avocado peptide extract | 2.000 |
| Dicaprylyl ether | 2.000 |
| Silanediol salicylate | 2.000 |
| Arachidic alcohol | 1.650 |
| Tromethamine | 1.180 |
| Cetyl alcohol | 1.000 |
| Salicylic acid | 1.000 |
| Ascorbyl glucoside | 1.000 |
| Glycine | 1.000 |
| Tocopheryl acetate | 1.000 |
| Behenyl alcohol | 0.900 |
| Squalane | 0.790 |

| | |
|---|---|
| Sodium citrate | 0.660 |
| PPG-12/SMDI Copolymer | 0.500 |
| Arachidyl glucoside | 0.450 |
| Perfume | 0.400 |
| *Sclerotium* gum | 0.160 |
| Cetearyl alcohol | 0.130 |
| Citric acid | 0.110 |
| Sepigel 305* | 0.100 |
| Preservative system | QS |

*A product which is marketed by the Seppic company

Anti-acneic Cream No 2

| | |
|---|---|
| Water | QSP 100% |
| Isononyl Isononanoate | 7.000 |
| Di-C$_{12-13}$ Alkyl malate | 7.000 |
| Isocetyl stearate | 5.000 |
| Butylene Glycol | 3.000 |
| *Oriza sativa* | 2.500 |
| Avocado peptide extract | 2.000 |
| C7 Sugars (heptitol) | 1.000 |
| Dicaprylyl Ether | 2.000 |
| Silanediol salicylate | 2.000 |
| Arachidic alcohol | 1.650 |
| Tromethamine | 1.180 |
| Cetyl alcohol | 1.000 |
| Salicylic acid | 1.000 |
| Ascorbyl Glucoside | 1.000 |
| Glycine | 1.000 |
| Tocopheryl acetate | 1.000 |
| Behenyl Alcohol | 0.900 |
| Squalane | 0.790 |
| Sodium citrate | 0.660 |
| PPG-12/SMDI Copolymer | 0.500 |
| Arachidyl Glucoside | 0.450 |
| Perfume | 0.400 |
| *Sclerotium* Gum | 0.160 |
| Cetearyl alcohol | 0.130 |
| Citric Acid | 0.110 |
| Sepigel 305* | 0.100 |
| Preservative system | QS |

*A product which is marketed by the Seppic company

Foaming Emulsion for Cleaning Atopic Skins

| | |
|---|---|
| Water | QSP 100 |
| Arlatone duo* | 20.00000 |
| Coco Glucoside | 12.00000 |
| Hydroxypropyl Guar | 2.00000 |
| Avocado peptide extract | 2.000 |
| Hydrogenated Glyceryl PEG-200 palmate | 1.10000 |
| Glyceryl PEG-7 Cocoate | 1.10000 |
| Silanediol salicylate | 1.00000 |
| Cocamide DEA | 1.00000 |
| Caprylol Glycine | 0.50000 |
| Potassium sorbate | 0.50000 |
| Polyquaternium 10 | 0.40000 |
| Perfume | 0.40000 |
| Citric acid | 0.30000 |
| Zinc PCA | 0.20000 |

*A product which is marketed by the Quimasso company.

Cleaning & Foaming Emulsion for Personal Hygiene

| | |
|---|---|
| Water | QSP 100 |
| Arlatone duo* | 20.00000 |
| Coco Glucoside | 12.00000 |
| Hydroxypropyl Guar | 2.00000 |
| Avocado peptide extract | 3.00000 |
| Avocado sugars | 1.00 |
| Lupine peptides | 2.00 |
| Hydrogenated Glyceryl PEG-200 Palmate | 1.10000 |
| Glyceryl PEG-7 Cocoate | 1.10000 |
| Silanediol salicylate | 1.00000 |
| Cocamide DEA | 1.00000 |
| Caprylol Glycine | 0.50000 |
| Potassium Sorbate | 0.50000 |
| Polyquaternium 10 | 0.40000 |
| Perfume | 0.40000 |
| Citric acid | 0.30000 |
| Zinc PCA | 0.20000 |

*A product which is marketed by the Quimasso company.

The invention claimed is:

1. A drug comprising:
0.1% to 20% by weight of an avocado peptide extract, and
0.001% to 30% by weight of D-mannoheptulose and/or perseitol in relation to the total weight of the drug, and
an appropriate excipient.

2. A method of treating a disease or disorder comprising administering to a patient in need thereof a drug according to claim 1, wherein said disease or disorder is selected from the group consisting of:
infections of the skin and phanerae,
inflammatory dermatoses, contact and/or atopic dermatitis, psoriasis, acne, itching dermatites;
diseases which are associated with a change in the Th1/Th2 balance;
diseases which are associated with a change in the synthesis of cytokines; or
burns.

3. The method according to claim 2, wherein said infections of the skin and phanerae are selected from the group consisting of folliculitis, furuncles, abscess, impetigo and whitlow.

4. The method according to claim 2, wherein said inflammatory dermatoses are atopic dermatitis.

5. The method according to claim 2, wherein diseases are associated with a change in the synthesis of IL-4 and/or IL-13.

6. The method according to claim 2, wherein said diseases are pathologies which are linked to a deficiency in the skin barrier, or pathologies linked to skins which have been weakened by an aggression from the environment.

7. The method according to claim 6, wherein diseases linked to a deficiency in the skin barrier are selected from the group consisting of hyperreactive, atopic, dry or aged skins.

8. A method for protection of skin in a patient in need thereof selected from the group consisting of:
immature newborn infants' or children's skin;
pathological immature newborn infants' or children's skin; and
healthy or pathological skin in adults or aged individuals;
comprising administering the drug of claim 1 to the patient.

9. A drug according to claim 1, wherein the avocado peptide extract is in an amount of 0.1-15 dry weight % in relation to the total weight of the drug.

10. A drug according to claim 1, wherein the avocado peptide extract is in an amount of 0.5-10 dry weight % in relation to the total weight of the drug.

11. A drug according to claim 1, wherein the avocado peptide extract is in an amount of 0.7-8 dry weight % in relation to the total weight of the drug.

12. A drug according to claim 1, wherein D-mannoheptulose and/or perseitol are in an amount of 0.01-20 dry weight % in relation to the total weight of the drug.

13. A drug according to claim 1, wherein D-mannoheptulose and/or perseitol are in an amount of 0.1-10 dry weight % in relation to the total weight of the drug.

14. A drug according to claim 1, wherein D-mannoheptulose and/or perseitol are in an amount of 0.5-5 dry weight % in relation to the total weight of the drug.

15. A drug according to claim 1, wherein the avocado peptide extract is obtained by a process comprising the following steps:
   a) obtaining an avocado cake by drying and removing oil from avocado fruit;
   b) cryogrinding and total delipidation of said cake, followed by decantation, centrifugation and collection of the cake;
   c) hydrolyzing the collected avocado cake in the presence of glucanases, followed by centrifugation and discarding of a soluble fraction formed thereby;
   d) hydrolyzing the glucanase hydrolyzed cake in the presence of one or several proteases, followed by centrifugation and discarding of residue formed thereby to provide a peptide phase;
   e) concentrating the peptide phase by nanofiltration; and
   f) simple filtrating (10 μm), followed by ultrafiltrating (cut-off limit 10 kD).

16. A drug according to claim 15, wherein following step e) and before step f), the process comprises a discoloration step in the presence of activated carbon.

17. A drug according to claim 15, wherein following step f) the process comprises a further step of addition of a preservative, a final sterilizing microfiltration (0.2 μm) and packaging.

18. A drug according to claim 15, wherein 50% by weight of peptides in the extract, are made up of 10-30 amino acids.

19. A drug according to claim 1, wherein the source of D-mannoheptulose and/or perseitol is a hydrosoluble extract of sugar of avocado.

20. A drug according to claim 19, wherein said hydrosoluble extract of sugar of avocado is obtained by a process comprising the following successive steps:
   a) obtaining an avocado oil cake, advantageously from the avocado fruit, by drying the avocado then extracting the lipids; then
   b) cryogenic grinding and total delipidation of said oil cake, then decanting and centrifuging so as to recover the soluble fraction rich in C7 sugars (elimination of the cake);
   c) demineralizing over an ionic resin of said soluble fraction obtained from the preceding step; then
   d) ultrafiltrating at 10000 daltons; and
   e) concentrating under vacuum and packaging.

21. The drug according to claim 20, wherein said hydrosoluble extract of sugars of the avocado comprises in weight, based on the total weight of the dry matter in the extract (relative composition determined by HPLC):
   D-mannoheptulose 5 to 80%,
   Perseitol 5 to 80%,
   Saccharose less than 10%,
   Glucose, less than 10%,
   Fructose, less than 10%.

* * * * *